United States Patent
Thierry et al.

[11] Patent Number: 5,756,122
[45] Date of Patent: May 26, 1998

US005756122A

[54] LIPOSOMALLY ENCAPSULATED NUCLEIC ACIDS HAVING HIGH ENTRAPMENT EFFICIENCIES, METHOD OF MANUFACTURER AND USE THEREOF FOR TRANSFECTION OF TARGETED CELLS

[75] Inventors: Alain Thierry; Anatoly Dritschilo, both of Bethesda, Md.

[73] Assignee: Georgetown University, Washington, D.C.

[21] Appl. No.: 483,090

[22] Filed: Jun. 7, 1995

[51] Int. Cl.$^6$ .................................................. A61K 9/127
[52] U.S. Cl. .................................. 424/450; 935/54
[58] Field of Search .......................... 424/450; 935/54, 935/52

[56] References Cited

U.S. PATENT DOCUMENTS

| | | | |
|---|---|---|---|
| 4,235,871 | 11/1980 | Papahadjopoulos et al. | 424/19 |
| 4,241,046 | 12/1980 | Papahadjopoulos et al. | 424/19 |
| 4,394,448 | 7/1983 | Szoka, Jr. et al. | 435/172 |
| 4,643,988 | 2/1987 | Segrest | 514/12 |
| 4,713,324 | 12/1987 | Fox | 435/4 |
| 4,762,720 | 8/1988 | Jizomoto | 424/450 |
| 4,789,633 | 12/1988 | Huang et al. | 435/240.2 |
| 4,902,512 | 2/1990 | Ishigami | 424/450 |
| 5,049,392 | 9/1991 | Weiner et al. | 424/450 |
| 5,094,785 | 3/1992 | Law | 264/43 |
| 5,223,263 | 6/1993 | Hostetler et al. | 424/450 |
| 5,227,170 | 7/1993 | Sullivan | 424/450 |

OTHER PUBLICATIONS

D. Lasic et al., "Liposomes Revisited", *Science* 267: 1275–1276 (1995).

G. Nabel et al., "Direct gene transfer with DNA–liposome complexes in melanoma Expression, biologic activity, and lack of toxicity in humans", *Proc. Natl. Acad. Sci. USA* 90: 11307–11311 (1993).

C. Wang et al., "pH–sensitive immunoliposomes mediate target–cell–specific delivery and controlled expression of a foreign gene in mouse", *Proc. Natl. Acad. Sci. USA* 84: 7851–7855 (1987).

P. Felgner et al., "Lipofection: A highly efficient, lipid–mediated DNA–transfection procedure", *Proc. Natl. Acad. Sci. USA* 84: 7413–7417 (1987).

Pinnaduwage in BBA 985, pp. 33–37 (1989.

*Primary Examiner*—Gollamudi S. Kishore
*Attorney, Agent, or Firm*—Foley & Lardner

[57] ABSTRACT

An improved method for encapsulating high molecular weight nucleic acids in liposomes, which provides for high nucleic acid entrapment efficiencies, is provided. The resulting compositions provide enhanced in vitro and in vivo transfection and are useful, for example, in producing cell lines expressing a desired nucleic acid sequence.

18 Claims, No Drawings

5,756,122

LIPOSOMALLY ENCAPSULATED NUCLEIC ACIDS HAVING HIGH ENTRAPMENT EFFICIENCIES, METHOD OF MANUFACTURER AND USE THEREOF FOR TRANSFECTION OF TARGETED CELLS

BACKGROUND OF THE INVENTION

Cells that express heterologous gene products are valuable as research tools, as "factories" for the production of gene products, and for gene therapy. It has therefore become increasingly important to be able to custom engineer cells with heterologous polynucleotide constructs rapidly and inexpensively. A major factor in the time and cost of generating such cells lines is the efficiency with which polynucleotides can be introduced and stably incorporated into the desired cells.

Currently, a variety of methods exist for transfecting polynucleotides into target cells. Such methods include conventional means such as calcium phosphate and polycation-mediated transfection, as well as protoplast fusion, viral and retroviral infection, microinjection and electroporation.

Another method recently investigated for delivery of polynucleotides into cells involves the administration of liposomally-encapsulated nucleic acids. Such methods originated in the early 1980's when Papahadjopoulos et al. disclosed the encapsulation of biologically-active materials, such as nucleic acids and proteins, in liposomes. These liposomes were then used for delivery of the biologically active materials to target cells. See, e.g., U.S. Pat. No. 4,241,046; U.S. Pat. No. 4,235,871; U.S. Pat. No. 4,394,448. See also, Lasic et al., *Science* 267:1275 (1995).

Such methods have been improved in order to enhance efficiency of the transfection process. For example, conjugating liposomes to ligands which selectively bind to targeted cells is known to enhance the efficiency of delivery to desired cells. Relevant patents which disclose the conjugation of liposomes to cell-targeting moieties, in particular, to antibodies, are e.g., U.S. Pat. No. 5,210,040; U.S. Pat. No. 4,957,735; U.S. Pat. No. 4,925,661; U.S. Pat. No. 4,806,466; U.S. Pat. No. 4,762,915; U.S. Pat. No. 4,708,933; U.S. Pat. No. 4,483,921; U.S. Pat. No. 4,480,041; U.S. Pat. No. 4,429,008.

pH-sensitive liposomes also provide for enhanced delivery of targeted nucleic acids into cells. For example, U.S. Pat. No. 4,789,633 and Huang et al., *Proc. Nat'l. Acad. Sci. USA* 87:7851 (1987) disclose pH-sensitive DNA containing liposomes which fuse with cell membranes at a pH below 7, thereby facilitating introduction of the desired DNA. While such liposomes enable improved delivery of foreign DNA's, they are still quite inefficient, generally because of poor entrapment efficiency. This poor entrapment efficiency means both that large quantities of DNA are wasted in preparing the liposomes, and that large quantities of liposomes must be used to achieve delivery of a given amount of DNA to cells.

Another method for achieving delivery of DNA containing liposomes involves the administration of complexes of DNA with cationic lipids. For example, U.S. Pat. No. 5,227,170 teaches encapsulation of oligonucleotides in cationic lipid complexes which further comprise a divalent cation solution containing the desired oligonucleotides and which have an osmolarity less than that of the internal aqueous phase. See also, Felgner et al., *Proc. Nat'l. Acad. Sci. USA*, 84:7413 (1987). Due to their cationic character, these liposomes can bind to serum proteins, thereby leading to inactivation of the oligonucleotides contained therein. Also, osmotic-dependent liposomes are known in the literature, i.e., as disclosed by U.S. Pat. No. 5,049,392.

Methods for optimizing the size of liposomes also are known. For example, U.S. Pat. No. 4,532,089 teaches a method for preparing giant liposomes. Also, U.S. Pat. No. 4,529,561 teaches a method for preparing liposomes in desired size ranges. Further, U.S. Pat. No. 5,223,263 teaches liponucleotide containing liposomes and the use thereof in delivery of the liponucleotides to desired cells.

Thus, it is clear that many methods for delivery of nucleic acids into cells are known in the art, as are methods which rely on liposomally-mediated introduction of nucleic acids. Conventional liposome encapsulation methods are subject to many constraints. For example, conventional methods for encapsulation of nucleic acids into liposomes are limited by poor entrapment efficiencies. That is, only a small percentage of the initial nucleic acid used actually becomes encapsulated. As discussed supra this is undesirable because it is inefficient both with respect to its use of DNA and with respect to the quantity of liposomes that must be used to deliver a given amount of DNA.

Also, most conventional methods for liposome encapsulation of nucleic acids are suitable only for encapsulation of small nucleotides, e.g., oligonucleotides. This is disadvantageous since expression of heterologous gene products in cells often requires the introduction of much larger DNA sequences that include not only coding regions, but also other cis-acting controls for regulating gene expression, such as promoter and enhancer sequences, operator sequences and the like, as well as a ribosome binding site, an initiation codon and transcription termination and polyadenylation signals. Buffer regions, origins of replication for extra-chromosomal replication, and flanking regions with homology to a target site for targeted chromosomal insertion by homologous recombination may also be included.

Present methods do not permit the efficient encapsulation of large DNA vectors such as plasmids and phagemids. This is particularly disadvantageous for those vectors that are designed to be maintained in an episomal state, i.e., extra-chromosomally. These vectors can avoid the potential problems which occur during non-targeted integration of a heterologous DNA into a host cell genome, e.g., oncogene activation, loss of recombined sequences, inactivation of essential genes, inefficient level of expression of the heterologous DNA or inadequate means for controlling level of gene expression. Large DNA vectors are also usually required when targeted integration into a chromosome by the method of homologous recombination is desired. This is because relatively large regions of flanking DNA are used to ensure that insertion occurs at a preferred chromosomal site, thereby avoiding the problems discussed supra associated with random insertion.

It is apparent, therefore, that a more efficient method of administering large DNA molecules into cells is greatly to be desired. In particular, it is desirable that an improved method of encapsulating high molecular weight nucleic acids into liposomes with high entrapment efficiencies is greatly to be desired.

SUMMARY OF THE INVENTION

Therefore, it is an object of the invention to provide a method for encapsulating high molecular weight nucleic acids and which also provides for high entrapment efficiency, in comparison to known methods for producing liposomally-encapsulated nucleic acids.

It is another object of the invention to provide a method for transfecting cells which is fast, inexpensive and reliable, in comparison to available methods for transfecting cells.

It yet is another object of the invention to provide a liposome comprising high molecular weight nucleic acids, e.g., comprising DNA's ranging from about 1.0 kB to about 20 kB, and preferably from about 5 to 18 kB.

In accomplishing the foregoing objects of the invention, there has been provided, in accordance with one aspect of the current invention, a method for encapsulating in liposomes nucleic acids ranging from about 1 to 20 kB and, preferably, from about 5 to about 18 kB, comprising the steps of (i) incubating a hydrated lipid film for an effective time at reduced temperature, where the hydrated lipid film is formed by addition of a concentrated aqueous solution of a high molecular weight nucleic acid to a dried lipid film; (ii) adding a minimum effective amount of phosphate buffered saline solution to the hydrated lipid film and vortexing for a time sufficient to generate liposomes and to swell the liposomes; and (iii) vortexing the resulting swelled liposomes. The method may also further comprise the step of (iv) removing unencapsulated nucleic acid from said liposomes by washing said liposomes. The washing may be achieved by centrifugation.

In accordance with another aspect of the invention, the lipid film comprises at least one lipid selected from the group consisting of dimyristoyl-diglycerol, phosphatidylethanolamine, phosphatidylcholine, phosphatidic acid, lysophosphatidylcholine, phosphatidylserine, sphingolipids, phosphatidylglycerol, sphingomyelin, cardiolipin, glycolipids, gangliosides, cerebrosides, cholesterol, tocopherol, and retinol.

In accordance with a further aspect of the invention the lipid film comprises dimyristoyldiglycerol, phosphatidylethanolamine and cholesterol, in a relative molar ratio of about 5:5:7 respectively.

In accordance with yet another aspect of the invention the nucleic acid solution has a concentration of 1–5 mg/ml, and the nucleic acid solution is added to the dried lipid film in a ratio of less than or equal to about 1.6 µl per mg of lipid. The effective time for the incubating step is preferably at least 12 hours, and the time for forming and swelling the liposomes is at least 30 minutes.

In accordance with still another aspect of the invention the size of the nucleic acid is preferably from about 1 kB to about 25 kB, or more preferably from about 5 kB to about 18 kB.

In accordance with a still further aspect of the invention there has been provided a method for transfecting cells comprising contacting a cell with an effective amount of swelled nucleic acid-containing liposomes, wherein the liposomes are prepared as described above. The nucleic acid is preferably a plasmid, a phagemid, or a cosmid.

In accordance with still another aspect of the invention there has been provided a liposome comprising a high molecular weight nucleic acid, produced by the method described above. In a preferred embodiment the nucleic acid has a size of at least 2 kB, and at least 25% of the liposomes contain the nucleic acid. In another preferred embodiment the nucleic acid has a size of at least 5 kB, and at least 10% of the liposomes contain the nucleic acid.

In accordance with yet aspect of the invention there has been provided a transfected cell prepared by the method described above. In a preferred embodiment the liposome contains a high molecular weight DNA encoding an antisense RNA, a ribozyme, or a therapeutic protein.

In accordance with a further aspect of the invention there has been provided a method for preparing a liposome-encapsulated nucleic acid comprising the steps of (i) incubating a hydrated lipid film for about 2 hours at about 4° C., wherein the hydrated lipid film is formed by addition of a concentrated aqueous solution of a high molecular weight nucleic acid to a dried lipid film in a ratio of less than or equal to about 1.6 µl of DNA solution per mg of lipid; (ii) adding a phosphate buffered saline solution to the hydrated lipid film in a ratio of less than or equal to about 1.6 µl per mg of lipid, and vortexing for a time sufficient to generate liposomes and to swell the liposomes; and (iii) vortexing the resulting swelled liposomes, whereby at least 25% of said liposomes contain the nucleic acid. In a preferred embodiment the high molecular weight DNA encodes a tissue-specific promoter.

In accordance with another aspect of the invention there is provided a liposome prepared by the methods described above, wherein the therapeutic protein is selected from the group consisting of platelet-derived growth factor, epidermal growth factor, interleukins 1–14, granulocyte colony stimulating factor, granulocyte-macrophage colony stimulating factor, tumor necrosis factor, leukemia inhibitory factor, amphiregulin, angiogenin, betacellulin, calcitonin, ciliary neurotrophic factor, brain-derived neurotrophic factor, neurotrophins 3 and 4, nerve growth factor, colony stimulating factor-1, endothelial cell growth factor, erythropoietin, acidic and basic fibroblast growth factor, hepatocyte growth factor, heparin binding EGF-like growth factor, insulin, insulin-like growth factors I and II, interferons α, β, and γ, keratinocyte growth factor, macrophage inflammatory protein α and β, midkine, oncostatin M, RANTES, stem cell factor, transforming growth factors α and β, and vascular endothelial growth factor.

DETAILED DESCRIPTION OF THE PREFERRED EMBODIMENTS

The present invention provides an improved method for the encapsulation of high molecular weight nucleic acids in liposomes, wherein a higher nucleic acid entrapment efficiency is achieved than can be achieved by conventional methods for encapsulating nucleic acids in liposomes. In the present invention, entrapment efficiency is defined as the percentage of the initial amount of the nucleic acid used which becomes encapsulated in the resulting liposomes.

This improved method also provides liposomal compositions in which a greater proportion of the liposomes actually contain the desired nucleic acids, than can be achieved with conventional methods for encapsulating nucleic acids in liposomes. Additionally, each liposome comprises a higher nucleic acid content, on average, than liposomes generated by conventional techniques.

These characteristics are advantageous for several reasons. First, the high encapsulation efficiency, which is generally at least 25%, and usually 50% based upon the initial amount of nucleic acid, but which may be as high or even higher than 90%, reduces cost since it requires less nucleic acid than conventional liposome encapsulation processes. Second, high entrapment efficiency improves the performance quality of the nucleic acid-containing liposomes because (i) a greater portion of the liposomes contain nucleic acid and (ii) the average nucleic acid content is higher than in liposomes generated by conventional methods. This translates into improved delivery of nucleic acids to target cells and, accordingly, there is a greater probability that a nucleic acid will be delivered to any given target cell. Because each nucleic acid delivered may not achieve stable transfection, a higher delivery rate improves the chance that a cell will be produced which expresses the desired product.

The present invention provides for the efficient encapsulation of high molecular weight polynucleotide molecules. The terms "nucleic acid" or "polynucleotide" as used herein are considered interchangeable unless otherwise indicated, and encompass DNA. RNA or a mixture of DNA and RNA. Nucleic acids according to the present invention may also include any strand structure. e.g., single-, double- or triple-stranded polynucleotide structures or mixtures thereof. Also, the nucleic acids may comprise a linear or circular structures, e.g., plasmids, phagemids, cosmids, etc.

As used herein, "high molecular weight" polynucleotide refers to a polynucleotide molecule that comprises at least one coding sequence that can be transcribed when the polynucleotide is introduced into a host cell. This transcription can produce an mRNA molecule that can then be translated to produce a polypeptide or protein, or it can produce an antisense RNA molecule. Transcription of the coding sequence of the HMW polynucleotide is preferably under the control of cis-acting regulatory elements, such as enhancer sequences, operator sequences and the like, and the polynucleotide also contains a ribosome binding site, an initiation codon and transcription termination and polyadenylation signals. The definition of HMW polynucleotides as used herein is, therefore, generally understood to mean polynucleotides that contain such regulatory elements. The HMW polynucleotide may also contain other elements such as origins of replication as are commonly found on polynucleotides used for transfection.

The present invention provides for the efficient encapsulation of large vectors, including those which contain sequences that permit stable, episomal maintenance and those which encode multigene cassettes. This is significant, in the case of episomal constructs, because integration of the desired nucleic acid into the host cell's genome may have a negative impact on the transfection process. For multigene cassettes, it also is important as coordinate regulation of the encoded genes can be more easily achieved.

The nucleic acids which may be encapsulated according to the present method may range in size from as small as about 500 bases to about 50 kilobases. In a preferred embodiment, the encapsulated nucleic acids will comprise DNA's ranging from about 1.0 to 25 kB and, preferably, from about 5 to about 18 kB.

The nucleic acids which may be encapsulated according to the present method may comprise sense or antisense polynucleotides. For example, antisense oligonucleotides may be encapsulated which selectively inhibit the expression of target DNA's. For example, antisense oligonucleotides may be encapsulated which are complementary to viral sequences and utilized for antiviral treatments, e.g., hepatitis, AIDS viral infection, papillomavirus infection, etc. The use of antisense oligonucleotides for genetic therapy has been reported in the literature. See Stein and Chang, Science 261: 1004 (1993). Also, ribozymal RNA's may be encapsulated and used to study gene expression or for genetic therapy.

In a preferred embodiment, the encapsulated nucleic acids will comprise an episomal element, e.g., a plasmid which contains one or more genes which are to be expressed in target cells. An episomal element containing an origin of replication that is recognized by the replication functions of the host cell will be stably maintained in the cell as an extrachromosomal element, thereby allowing stable expression of genes encoded on the element. In general, these genes will cause the target cell to produce a heterologous expression product, or acquire an altered phenotype. If the episomal element does not contain an origin or replication that is recognized by the host cell, the expression product will be produced only transiently.

Another utility for the subject liposomal encapsulated nucleic acids will comprise producing cells or animals which express a defective gene or genes. Thereby, the resulting cells or animals may be used as in vitro or in vivo models for assessing the efficacy of potential therapeutic agents.

A further utility for the liposomally encapsulated nucleic acids of the invention is for gene therapy, that is for introducing into cells DNA constructs that encode a therapeutic product. The therapeutic product can be, for example, an antisense RNA or ribozyme RNA molecule, or it can be a therapeutic protein. A "therapeutic protein" as used herein refers to a peptide, polypeptide, or protein that, when confers a therapeutic benefit to a host when administered to the host, or when it is expressed in cells of the host. The gene therapy can be in vivo, in which the liposomally encapsulated DNA constructs are introduced directly into a host animal, preferably a human, or can be ex vivo, in which isolated cells are first transfected with the liposomally encapsulated DNA constructs, and are then reintroduced into a host animal. Ex vivo gene therapy in humans is described in U.S. Pat. No. 5,399,346, which is hereby incorporated by reference in its entirety. See also Tolstoshev, Annu. Rev. Pharmacol. Toxicol. 33:573–96 (1993), for a general review of gene therapy, which is also incorporated herein by reference in its entirety.

The subject nucleic acid containing liposomes will, in general, be made by a method comprising:

(i) forming a lipid film under reduced pressure, (ii) hydrating the lipid film by the addition of an effective amount of a nucleic acid containing solution;

(iii) incubating the mixture for an effective time period at reduced temperature;

(iv) adding a phosphate buffered solution to the hydrated lipid film and vortexing;

(v) incubating at ambient temperature for a time sufficient to facilitate swelling; and (vi) vortexing the resultant swelled composition to produce nucleic acid containing liposomes.

Typically, there will be an intervening step between step (iv) and step (v) wherein additional phosphate buffered saline solution is added and the mixture is again vortexed. Also, after step (vi), the unencapsulated (free) nucleic acids typically will be removed. This may be effected, for example, by washing the liposomes repeatedly while centrifuging in a phosphate buffered saline solution.

In general, about 20 μmole (about 0.64 mg) of lipid is dried under reduced pressure (30 mm Hg) in a 40 mm² surface of a round-bottom glass flask or tube. The resulting dry lipid film is hydrated with about 1.4 μl of aqueous solution containing DNA to be encapsulated. Generally, a container having a mean surface area of about 10 to 200 mm² is used, under a reduced pressure of about 1 to 50mm Hg, and a hydration volume of about 0.7 to 2 μl.

Step (i) typically will be effected by forming a lipid film using any lipid or mixture of suitable lipids which are evaporated under a vacuum. The lipid mixture used to make this lipid film will comprise any lipid or mixture of lipids which provides for suitable nucleic acid entrapment efficiency.

Examples of lipids suitable for use in the invention include, e.g., known vesicle or liposome forming compounds such as phosphatidylcholine, both naturally occurring and synthetically prepared, phosphatidic acid, lysophosphatidylcholine, phosphatidylserine, phosphatidyl ethanolamine, sphingolipids, phosphatidylglycerol, sphingomyelin, cardiolipin, glycolipids, gangliosides, and cerebrosides such as soybean phospholipids. Other suitable lipids include steroids, cholesterol, aliphatic amines such as long chain aliphatic amines and carboxylic acids, long chain sulfates and phosphates, diacetyl phosphates, butylated hydroxy toluene, tocopherol, retinol and isoprenoid compounds which may confer desired properties to the formed liposomes.

Also, synthetic phospholipids containing either altered aliphatic portions such as hydroxyl groups, branched carbon chains, cyclo derivatives, aromatic derivatives, ethers, amides, polyunsaturated derivatives, halogenated derivatives or altered hydrophilic portions containing carbohydrate, glycol, phosphate, phosphamide, quaternary amines, sulfate, sulfonyl, carboxy, amine, sulphydryl, imidazole groups and combinations of such groups can be either substituted or intermixed with the above-mentioned lipids which may be used in the present invention. Lipids suitable for use in preparing liposomes are well known in the literature, and are described, e.g., in U.S. Pat. No. 4,201,767; U.S. Pat. No. 4,235,877; U.S. Pat. No. 4,241,046; U.S. Pat. No. 4,261,975; and U.S. Pat. No. 4,394,448, all of which are incorporated by reference in their entireties.

The present invention embraces the use of any lipid or combination which provides the desired encapsulation efficiency which, in general, will be at least about 25%, relative to the initial amount of nucleic acid used for encapsulation. In a preferred embodiment the encapsulation efficiency will be preferably at least 50%, more preferably 70%, and still more preferably will be in the range from about 70% to about 90%.

Preferred lipids include dimyristoyl phosphatidyl glycerol, cardiolipin, phosphatidyl choline, phosphatidyl glycerol, sphingomyelin, and cholesterol. In a particularly preferred embodiment, the lipids used to make the lipid film comprise a mixture of dimyristoyldiglycerol, phosphatidylethanolamine and cholesterol. Most preferably, the molar ratio of these lipids is about 5:5:7 of dimyristoyldiglycerol, phosphatidylethanolamine and cholesterol, respectively.

Step (ii), the hydration step, in general, comprises the addition of an effective amount of a nucleic acid-containing aqueous solution to a dried lipid film. Preferably, this solution will comprise a highly concentrated, aqueous, nucleic acid solution and, more preferably, a concentrated DNA containing solution. A preferred concentration range for the DNA solution is from about 1 mg/ml to about 5 mg/ml, but concentrations outside this range may also be used, for example form about 0.01 mg/ml to about 20 mg/ml, or up until the DNA solution is saturated. In the examples, the solution comprises plasmids in an aqueous solution at a concentration of about 1–2 mg/ml. This concentrated nucleic acid solution is added to the dry lipid film in an amount sufficient to provide hydration and to achieve the desired amount of nucleic acid encapsulation.

For example, in one instance, a 2 mg/ml DNA plasmid solution was utilized, at 1.6 µl solution/mg lipid, to facilitate hydration. This amount may be varied as needed. A suitable amount of the nucleic acid-containing solution will vary from about 1.7 to 17 µg of DNA per mg of lipid if utilizing a nucleic acid solution having a concentration of about 1–5 mg/ml of DNA.

As discussed supra, the nucleic acid contained in this solution may comprise DNA, RNA or a mixture thereof, and may comprise linear or circular structures. Also, the encapsulated nucleic acids may be single or multi-stranded and may comprise sense or antisense nucleic acid sequences. In the preferred embodiment, the nucleic acids will comprise DNA constructs having a size ranging from about 5 to about 18 kilobases. In general, such DNA constructs will contain a gene or genes which are to be expressed in the targeted cells. The DNA construct also preferably will contain suitable regulatory sequences which provide for the expression of these genes, in addition to sequences that provide for these DNA constructs to autonomously replicate in target cells if necessary, and also suitable selectable markers, e.g., antibiotic resistance markers. In general, these genes will be expressed under the control of regulatable promoters.

In the most preferred embodiments, the DNA constructs will contain a gene or genes which produce a therapeutic or valuable gene product. Examples of such gene products include, but are not limited to, therapeutic lymphokines, cytokines, hormones, cell adhesion molecules, enzymes or enzyme inhibitors, receptors, ion channels, transcription factors, protein kinases, protein phosphatases, and cellular antigens for generating an immune response in a host. Alternatively the DNA constructs will contain suicide genes, tumor suppressor genes, genes encoding antisense RNAs, or genes that induce or prevent cellular apoptosis.

Examples of lymphokines and cytokines that can be encoded by the liposomally-encapsulated DNA constructs of the invention include platelet-derived growth factor, epidermal growth factor, interleukins 1–14, granulocyte colony stimulating factor, granulocyte-macrophage colony stimulating factor, tumor necrosis factor, leukemia inhibitory factor, amphiregulin, angiogenin, betacellulin, calcitonin, ciliary neurotrophic factor, brain-derived neurotrophic factor, neurotrophins 3 and 4, nerve growth factor, colony stimulating factor-1, endothelial cell growth factor, erythropoietin, acidic and basic fibroblast growth factor, hepatocyte growth factor, heparin binding EGF-like growth factor, insulin, insulin-like growth factors I and II, interferons α, β, and γ, keratinocyte growth factor, macrophage inflammatory protein α and β, midkine, oncostatin M, RANTES, stem cell factor, transforming growth factors α and β, and vascular endothelial growth factor. Examples of cell adhesion molecules include integrins, cadherins, selecting, and adhesion molecules of the immunoglobulin superfamily, such as VCAM, ICAM, PECAM, and NCAM. Examples of tumor suppressor genes include p53, DCC, Rb, and MTS1. Those of skill in the art will recognize that other genes can also be used in the invention.

In addition, as discussed supra, the DNA construct will contain regulatory elements that can control replication of the construct within the cell, as well as transcription and translation of genes encoded on the construct. For use in in vivo gene therapy it is sometimes useful for these regulatory elements to be tissue specific. The term "tissue-specific promoter" or "tissue-specific transcriptional regulatory sequence" or indicates a transcriptional regulatory sequence, promoter and/or enhancer that is induced selectively or at a higher level in cells of the target tissue than in other cells. For example, tumor cell-specific promoters include promoters that are induced selectively or at a higher level in a particular cell type or a tumor cell. Tissue specific promoters are known in the art. Examples include: the alpha-actin promoter (Shani, *Mol. Cell. Biol.*, 6:2624 (1986)); the elastase promoter (Swift et al., *Cell*, 38:639 (1984)); the alpha-fetoprotein promoter (Krumlauf et al., *Nature*, 319:224–226 (1985)); the beta-globin promoter, (Townes et al., *EMBO J.*, 4:1715 (1985)); the human growth hormone promoter (Behringer et al., *Genes Dev.*, 2:453 (1988)); the insulin promoter (Selden et al., *Nature*, 321:545 (1986)) and a prostate-specific promoter (Allison et al., *Mol. Cell. Biol.*, 9:2254 (1989).

Step (iii) of the subject method comprises incubating the hydrated lipid film for about 12 to 24 hours at a reduced temperature, for example at about 4° C.

Step (iv) will in general comprise the addition of a minimum effective amount of a phosphate buffered saline solution followed by vortexing. This minimum effective amount of the added phosphate buffer solution will be less than about 1.6 µl/mg of lipid, and preferably will range from about 0.5 to 1.5 µl/mg lipid. In the exemplified embodiment, 1.4 µl of phosphate buffered saline solution was added per mg of the hydrated lipid.

In most cases, the initial vortexing will be followed by another step wherein additional phosphate buffered saline solution is added followed by vigorous vortexing. This may be effected by the addition of a second phosphate buffered saline solution in an amount less than about 1.6 µl/mg of lipid, and preferably from about 0.5 to about 1.5 µl/mg lipid.

Step (v) comprises incubating the mixture obtained from step (iv) for a time sufficient to permit swelling and, thereafter, generation of liposomes. In general, this will comprise incubating the mixture at ambient temperature for at least about 30 minutes, and preferably at least about 2 hours. In the exemplified embodiment, the swelling time was 2 hours. Those of skill in the art will recognize, however, that this time may be varied with only routine experimentation to optimize the formation of liposomes. Additional PBS solution (8 µl/mg of lipid) may optionally be added at this point to dilute the liposome solution.

Step (vi) comprises homogenization and resuspension of the swelled liposome composition, usually by vortexing. With liposomes containing smaller oligonucleotides this step is conveniently and efficiently carried out by sonication of the liposome mixture. This procedure is not suitable, however, for liposomes containing larger DNA constructs, which degrade rapidly under sonication conditions. It has been found, unexpectedly, that thorough mixing, homogenization and resuspension can be achieved by vortexing the liposome mixture.

As discussed supra, after the nucleic acid-containing liposomes are produced, the composition preferably will be treated to remove the free nucleic acids. This may be effected by any suitable method which does not adversely affect the liposomes, for example, by washing the liposomes in a suitable solution, e.g., phosphate buffered saline, followed by centrifugation.

Nucleic acid-containing liposomes produced in this manner may be used immediately or may be stored under favorable conditions, e.g., at about 4° C. Liposomes according to the present invention are stable for up to three weeks.

After the liposomes are produced, the encapsulation efficiency may be ascertained by known methods. For example, a DNA sample containing radiolabeled plasmid DNA constructs can be employed. This permits determination of the relative amounts of liposome-contained and free radioactivity.

The subject method reliably provides for nucleic acid entrapment efficiencies ranging from at least 25 to 50%, and more typically about 70 to 90% based upon the initial amount of nucleic acid contained in the sample, e.g., a DNA plasmid containing sample.

These liposomes may be used for both in vitro or in vivo transfection of nucleic acids into targeted cells. The targeted cells can be any cell whose cellular membrane is comprised of a lipid bilayer, and in general will comprise eukaryotic cells, and preferably mammalian cells, more preferably murine or human cells.

If the subject liposomes are to be administered in vivo, it may be preferable to conjugate these liposomes to a moiety which provides for the liposome to bind to targeted cells. Examples of such targeting moieties will include antibodies, or ligands which selectively bind to the targeted cells. Methods for conjugating liposomes to targeting moieties, e.g., antibodies are well known in the art and are discussed, supra. For example, the subject liposomes may be conjugated to an antiviral antibody if the liposomes contain an antiviral construct, e.g., a nucleic acid which encodes a gene product which renders transfected cells susceptible to a particular drug.

If transfection is effected in vitro, a suitable amount of the subject liposomes will be added to a cell culture medium containing the targeted cells. A suitable amount of the liposome composition may range from about 0.12 to 1.2 mg of liposome per $10^6$ cells, or from about 0.1 to about 10 µg of encapsulated DNA per $10^6$ cells. Those of skill in the art will realize, however, that this amount can vary, depending upon factors such as the lability of the particular targeted cell, its resistance to transfection, whether the liposomes contain smaller or larger nucleic acids, the activity of the particular gene, and the desired level of gene expression.

The resulting liposomally-transfected cells may be used for various applications. For example, the cells may be used to express a polypeptide encoded by the incorporated nucleic acids, e.g., a desired mammalian gene product. Also, if the incorporated nucleic acids result in the cells expressing a particular genetic defect, the cells may be used as models for studying the efficacy of proposed therapies for the particular genetic defect.

Alternatively, if in vitro liposomal transfection results in the incorporation of genes which compensate for some genetic defect, or which encode a moiety such as an antisense RNA, ribozyme, or therapeutic protein, these cells may be administered to a host in need of genetic therapy. See U.S. Pat. No. 5,399,346.

If the nucleic acid-containing liposomes are to be used in vivo, they are administered to a host in need of genetic therapy. Another variation on in vivo use is for the generation of genetic defects, e.g., transgenic or "knock-out" mice which are useful in the study of disease. An example of genetic therapy in a patient is when a DNA construct encoding human leukocyte antigen B7 (HLAB7) is encapsulated in a liposome as described supra and injected directly into the tumor lesions of a patient suffering from cutaneous melanoma, as described in Nabel et al., *Proc. Natl. Acad. Sci.* 90:11307 (1993), which is hereby incorporated by reference in its entirety. The HLAB7 stimulates the host immune response against the melanoma cells.

Generally, an in vivo liposomal dosage will range from about 0.2 to 20 mg/kg of body weight, and preferably from about 2 mg to 10 mg/kg of body weight. The amount will, of course, depend on the particular genetic defect, the type of nucleic acid encapsulated, the desired level of gene expression, the amount of nucleic acid contained in the liposomes, and other factors as discussed supra.

A particular advantage of the present invention is that it provides for the delivery of episomal elements to targeted cells, e.g., DNA plasmids. Preferably, the liposomes will be conjugated to a targeting moiety, e.g., an antibody to enhance delivery, when the desired target is an in vivo one, e.g., a tumor. This will avoid some of the problems which occur via integration of heterologous nucleic acids into normal host cell genomes.

Liposome compositions according to the present invention may be administered with additional substances, e.g., pharmaceutical carriers and excipients. Suitable carriers or excipients are described in REMINGTON'S PHARMACEUTICAL SCIENCES: DRUG RECEPTORS AND RECEPTOR THEORY, (18th ed.), Mack Publishing Co., Easton, Pa. (1990). The choice of carrier, diluent, excipient, etc. will depend upon the desired mode of delivery. The liposomal compositions of the invention can be administered by any route currently known for delivering polynucleotide molecules to cells, including, but not limited to intravenous or intramuscular injection, transdermally as a component of an ointment or cream, intratracheally, intranasally, or orally by aerosol or by drip, rectally, etc. Preferably, however, the liposomes will be administered by injection.

Additionally, liposomes according to the present invention may be administered in vivo in combination with other medicaments suitable for use in treating a particular disorder. For example, if the liposomes contain a "suicide gene" which renders targeted cells susceptible to a particular drug, it may be desirable to coadminister liposomes in with the drug. The drug may be, but need not be, liposomally encapsulated.

The efficiency of in vivo or in vitro transfection may be measured by standard methods. See Sambrook et al., MOLECULAR CLONING: A LABORATORY MANUAL, Second Edition, Cold Spring Harbor Laboratory, Cold Spring Harbor, N.Y. (1989). For example, the expression of genes encoded on a liposomally encapsulated DNA construct transfected into cells in vitro can be studied by Northern blotting or RNA PCR to measure production of RNA transcripts, and by Western blotting, immunoprecipitation, and in situ immunohistochemistry to detect and measure protein production. Integration of the DNA into the host cell chromosome can be determined by PCR or by Southern blotting. The same methods are used to determine whether tissue treated in vivo contains transfected genes, or is expressing gene products of the transfected genes. This is preferably carried out on a biopsy sample of the tissue of interest.

The present invention, thus generally described, will be understood more readily by reference to the following examples, which are provided by way of illustration and are not intended to be limiting of the present invention.

EXAMPLE 1

Preparation of Liposomally Encapsulated DNA

Liposome-encapsulated DNA was prepared by thin lipid hydration using a highly concentrated DNA solution. Specifically, dimyristoylphosphatidyldiglycerol, phosphatidylethanolamine, and cholesterol were mixed at a 5:5:7 molar ratio in a round-bottom flask, with a total weight of 6.4 mg. A thin lipid film was formed by rotary evaporation under vacuum. The resultant dry lipid film was then hydrated by adding 10 µl of a 2 mg/ml solution of $^{32}$P-labeled plasmid DNA. The hydrated lipid film was then incubated overnight at 4° C. After this incubation period, 10 µl of phosphate buffer saline (PBS) were added to the hydrated lipid film and the mixture was vortexed. After vortexing, supplemental PBS was added, specifically 1.4 µl/mg lipid of PBS, and the mixture was vigorously vortexed. This vortexed composition was then allowed to swell for 2 hours at room temperature and the resulting liposome containing suspension was vortexed. On some occasions, additional PBS (8 µl/mg of lipid) was then added if necessary. Free (unencapsulated) DNA was then removed by washing the liposomes by centrifugation (3× at 70,000 g for 30 minutes) in PBS.

The encapsulation efficiency was then determined by counting the radioactivity comprised in an aliquot of a liposomal DNA preparation. The entrapment rate was found to be 70–90% based upon the initial counts. Moreover, this result was reliably reproducible in additional trials.

EXAMPLE 2

In vitro Transfection of Mammalian Cells Using Liposomally Encapsulated DNA Plasmids Squamous carcinoma SCC 35 cells were transfected with plasmids pSV40neo and pRSVcat which contain the neomycin resistance gene and the chloramphenicol acyltransferase gene, respectively. These plasmids were chosen to allow measurement of the efficiencies of transient and stable transfection of cells transfected by various transfection methods.

pSV40neo (Promega Corp., Madison, Wis.) contains a gene for neomycin resistance, thereby allowing transfected cells that express the gene product to survive in culture in medium containing neomycin. When the culture is maintained long-term in neomycin, the only cells that survive are ones that have stably integrated the neo gene into their chromosomes.

pRSVcat (Promega Corp., Madison, Wis.) contains a gene encoding chloramphenicol acyltransferase. The level of transient expression of the cat gene in cells that are transfected with pRSV cat was measured with a standard CAT assay.

Table 1 compares the results obtained after transfecting SCC 35 cells with pSV40neo and pRSVcat using the minimum volume entrapment (MVE) liposomal transfection method of the present invention, with the results obtained with DEAE-dextran under standard conditions, with calcium phosphate under standard condition, and with a commercially available cationic lipid reagent (Lipofectin, Life Technologies, Gaithersburg, Md.) under conditions recommended by the manufacturer.

TABLE 1

Transfection Efficiency:
MVE-Liposomes Compared with
Conventional Methods

| | Relative Transfection Efficiency Units | |
|---|---|---|
| Method | Stable Transfection[1] | Transient Transfection[2] |
| DEAE-dextran | 1 | 1 |
| Calcium phosphate | 1.7 | 7.5 |
| Lipofectin ™ reagent (Life Technologies) | 2.3 | ND |
| MVE Liposomes | 7 | 14 |

[1]Stable transfection efficiency was determined by selecting in G418 containing medium squamous carcinoma SCC 35 cells transfected with pSV40 neo plasmid.
[2]Transient transfection efficiency was ascertained following transfection of SCC 35 cells with pRSV cat plasmid and identification by immunofluorescence of cells producing CAT protein.

These results demonstrate that nucleic acids encapsulated in liposomes according to the present invention provide for greatly enhanced transfection efficiencies relative to other available techniques, e.g., DEAE-dextran, calcium phosphate and Lipofectin™ reagent mediated transfection. While not wishing to be bound by any theory of mechanism of action, the present inventors believe that the enhanced transfection efficiencies seen with the method of the present invention are attributable to its high encapsulation efficiency, which provides a liposome population in which a very high percentage of the liposomes contain encapsulated nucleic acids.

EXAMPLE 3

Cellular Uptake of Liposomally Encapsulated Plasmid DNA

Plasmid DNA (18 kb) was nick translated with $^{35}S$ under standard conditions. See Sambrook et al., MOLECULAR CLONING: A LABORATORY MANUAL, Second Edition, (Cold Spring Harbor Laboratory Press, Cold Spring Harbor, N.Y. 1989). This DNA was then encapsulated in liposomes as described in Example 1. The liposomes were constituted from dimyristoyl phosphatidylglycerol, phosphatidylethanolamine and cholesterol in a 5:5:7 ratio, as described in Example 1. This liposomal solution was added to a culture of SCC35 squamous cell carcinoma cells seeded in microchamber glass slides, at a final liposome concentration of 1 µM. The cells were than incubated for 24 h, after which they were washed and then subjected to emulsion autoradiography. This showed a dense array of black dots, corresponding to the presence of radioactively labeled plasmid DNA, in the intracellular compartment and surrounding the cell surface. These results demonstrated that liposomal DNA was effectively taken up by the cells, and penetrated to the cell cytoplasm.

All publications and patent applications mentioned in this specification are indicative of the level of skill of those in the art to which the invention pertains. Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method for preparing a liposome-encapsulated nucleic acid, comprising the steps of:
   (i) incubating a hydrated lipid film for an effective time at reduced temperature, wherein said hydrated lipid film is formed by addition of a concentrated aqueous solution of a high molecular weight nucleic acid to a dried lipid film, wherein the size of said nucleic acid is from about 1 kB to about 25 kB, and wherein said nucleic acid solution has a concentration of 1-5 mg/ml and is added to said dried lipid film in a ratio of less than or equal to about 1.6 µl per mg of lipid;
   (ii) adding a minimum effective amount of phosphate buffered saline solution to the hydrated lipid film and vortexing for a time sufficient to generate liposomes and to swell said liposomes; and
   (iii) vortexing the resulting swelled liposomes.

2. The method according to claim 1, wherein said lipid film comprises at least one lipid selected from the group consisting of dimyristoyl-diglycerol, phosphatidylethanolamine, phosphatidylcholine, phosphatidic acid, lysophosphatidylcholine, phosphatidylserine, sphingolipids, phosphatidylglycerol, sphingomyelin, cardiolipin, glycolipids, gangliosides, cerebrosides, cholesterol, tocopherol, and retinol.

3. The method according to claim 2, wherein said lipid film comprises dimyristoyldiglycerol, phosphatidylethanolamine and cholesterol, in a relative molar ratio of about 5:5:7 respectively.

4. The method according to claim 1, wherein said effective time for the incubating step is at least 12 hours.

5. The method according to claim 4, wherein said time for forming and swelling said liposomes is at least 30 minutes.

6. The method according to claim 1, wherein the size of said nucleic acid is from about 5 kB to about 18 kB.

7. The method according to claim 1, wherein the method further comprises the step of (iv) removing unencapsulated nucleic acid from said liposomes by washing said liposomes.

8. The method according to claim 7, wherein said washing is achieved by centrifugation.

9. A method for transfecting cells comprising contacting a cell with an effective amount of swelled nucleic acid-containing liposomes, wherein said liposomes are prepared by the steps of:
   (i) incubating a hydrated lipid film for an effective time at reduced temperature, wherein said hydrated lipid film is formed by addition of a concentrated aqueous solution of a high molecular weight nucleic acid to a dried lipid film, wherein the size of said nucleic acid is from about 1 kb to about 25 kB, and wherein said nucleic acid solution has a concentration of 1-5 mg/ml and is added to said dried lipid film in a ratio of less than or equal to about 1.6 µl per mg of lipid;
   (ii) adding a minimum effective amount of phosphate buffered saline solution to the hydrated lipid film and vortexing for a time sufficient to generate liposomes and to swell said liposomes; and
   (iii) vortexing the resulting swelled liposomes.

10. The method according to claim 7, wherein said nucleic acid is a plasmid, a phagemid, or a cosmid.

11. A liposome comprising a high molecular weight nucleic acid, produced by the method of claim 1.

12. A liposome preparation comprising a nucleic acid having a size of at least 2 kB, wherein at least 25% of said liposomes contain said nucleic acid, and wherein said liposome preparation is obtainable by:
   (i) incubating a hydrated lipid film for an effective time at reduced temperature, wherein said hydrated lipid film is formed by addition of a concentrated aqueous solution of a high molecular weight nucleic acid to a dried lipid film, wherein the size of said nucleic acid is from about 1 kB to about 25 kB, and wherein said nucleic acid solution has a concentration of 1-5 mg/ml and is added to said dried lipid film in a ratio of less than or equal to about 1.6 µl per mg of lipid;
   (ii) adding a minimum effective amount of phosphate buffered saline solution to the hydrated lipid film and vortexing for a time sufficient to generate liposomes and to swell said liposomes; and
   (iii) vortexing the resulting swelled liposomes.

13. A liposome preparation comprising a nucleic acid having a size of at least 5 kB, wherein at least 10% of said liposomes contain said nucleic acid, and wherein said liposome preparation is obtainable by:
   (i) incubating a hydrated lipid film for an effective time at reduced temperature, wherein said hydrated lipid film is formed by addition of a concentrated aqueous solution of a high molecular weight nucleic acid to a dried lipid film, wherein the size of said nucleic acid is from about 1 kB to about 25 kB, and wherein said nucleic acid solution has a concentration of 1-5 mg/ml and is added to said dried lipid film in a ratio of less than or equal to about 1.6 µl per mg of lipid;

(ii) adding a minimum effective amount of phosphate buffered saline solution to the hydrated lipid film and vortexing for a time sufficient to generate liposomes and to swell said liposomes; and (iii) vortexing the resulting swelled liposomes.

14. A transfected cell prepared by the method of claim 9.

15. A liposome prepared by the method of claim 1, wherein said high molecular weight DNA encodes an antisense RNA, a ribozyme, or a therapeutic protein.

16. A method for preparing a liposome-encapsulated nucleic acid comprising the steps of:

(i) incubating a hydrated lipid film for about 2 hours at room temperature, wherein said hydrated lipid film is formed by addition of a concentrated aqueous solution of a high molecular weight nucleic acid to a dried lipid film in a ratio of less than or equal to about 1.6 µl of DNA solution per mg of lipid, wherein said nucleic acid has a size between about 1 kB and about 25 kB, and wherein said nucleic acid solution has a concentration of 1–5 mg/ml;

(ii) adding a phosphate buffered saline solution to the hydrated lipid film in a ratio of less than or equal to about 1.6 µl per mg of lipid, and vortexing for a time sufficient to generate liposomes and to swell said liposomes; and (iii) vortexing the resulting swelled liposomes, whereby at least 25% of said nucleic acid is incorporated in said liposomes.

17. A liposome according to claim 15, wherein said therapeutic protein is selected from the group consisting of platelet-derived growth factor, epidermal growth factor, interleukins 1–14, granulocyte colony stimulating factor, granulocyte-macrophage colony stimulating factor, tumor necrosis factor, leukemia inhibitory factor, amphiregulin, angiogenin, betacellulin, calcitonin, ciliary neurotrophic factor, brain-derived neurotrophic factor, neurotrophins 3 and 4, nerve growth factor, colony stimulating factor-1, endothelial cell growth factor, erythropoietin, acidic and basic fibroblast growth factor, hepatocyte growth factor, heparin binding EGF-like growth factor, insulin, insulin-like growth factors I and II, interferons $\alpha$, $\beta$, and $\gamma$, keratinocyte growth factor, macrophage inflammatory protein $\alpha$ $\beta$, and $\gamma$ midkine, oncostatin M, RANTES, stem cell factor, transforming growth factors $\alpha$ and $\beta$, and vascular endothelial growth factor.

18. A liposome according to claim 15, wherein said high molecular weight DNA further encodes a tissue-specific promoter operatively linked to said antisense RNA, ribozyme, or therapeutic protein.

* * * * *